United States Patent
Li et al.

(10) Patent No.: US 11,389,101 B2
(45) Date of Patent: Jul. 19, 2022

(54) METHOD AND DEVICE FOR IDENTIFYING ARRHYTHMIA, AND COMPUTER READABLE MEDIUM

(71) Applicant: BOE TECHNOLOGY GROUP CO., LTD., Beijing (CN)

(72) Inventors: Guangfei Li, Beijing (CN); Yang Han, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 35 days.

(21) Appl. No.: 16/448,224

(22) Filed: Jun. 21, 2019

(65) Prior Publication Data
US 2020/0015695 A1 Jan. 16, 2020

(30) Foreign Application Priority Data
Jul. 13, 2018 (CN) .......................... 201810770314.8

(51) Int. Cl.
| | |
|---|---|
| A61B 5/35 | (2021.01) |
| A61B 5/364 | (2021.01) |
| A61B 5/352 | (2021.01) |
| A61B 5/366 | (2021.01) |
| A61B 5/00 | (2006.01) |

(52) U.S. Cl.
CPC ............... *A61B 5/364* (2021.01); *A61B 5/35* (2021.01); *A61B 5/352* (2021.01); *A61B 5/366* (2021.01); *A61B 5/726* (2013.01); *A61B 5/7267* (2013.01)

(58) Field of Classification Search
CPC ..................... A61B 5/0452–0472; A61B 5/726
See application file for complete search history.

(56) References Cited

U.S. PATENT DOCUMENTS

| | | | | |
|---|---|---|---|---|
| 10,194,821 | B2* | 2/2019 | Habte | A61B 5/316 |
| 2008/0109041 | A1* | 5/2008 | de Voir | A61N 1/37 |
| | | | | 607/7 |
| 2008/0167567 | A1* | 7/2008 | Bashour | A61B 5/7267 |
| | | | | 600/518 |

(Continued)

FOREIGN PATENT DOCUMENTS

| | | |
|---|---|---|
| CN | 105832328 A | 8/2016 |
| CN | 107137077 A | 9/2017 |
| CN | 107657318 A | 2/2018 |

OTHER PUBLICATIONS

1st Office Action dated Jul. 28, 2020 for Chinese Patent Application No. 201810770314.8.

*Primary Examiner* — Michael W Kahelin
*Assistant Examiner* — Michael A Rizzuto
(74) *Attorney, Agent, or Firm* — Perilla Knox & Hildebrandt LLP; Kenneth A. Knox

(57) ABSTRACT

The present application discloses a method for identifying arrhythmia, a device for identifying arrhythmia, and a computer readable medium. The method includes: acquiring a type of arrhythmia to be identified; acquiring an ECG signal collected by an ECG acquisition device; detecting feature wave information in the ECG signal according to the type of arrhythmia to be identified; extracting a feature parameter from the denoised ECG signal and the feature wave information according to the type of arrhythmia to be identified; and identifying, by a classifier, an occurrence of the type of arrhythmia to be identified according to the feature parameter.

12 Claims, 4 Drawing Sheets

(56) References Cited

U.S. PATENT DOCUMENTS

2014/0148714 A1* 5/2014 Mamaghanian ..... A61B 5/0404
 600/509
2015/0164349 A1* 6/2015 Gopalakrishnan ..... A61B 5/361
 600/508

* cited by examiner

METHOD AND DEVICE FOR IDENTIFYING ARRHYTHMIA, AND COMPUTER READABLE MEDIUM

CROSS REFERENCE TO RELATED APPLICATIONS

The present application is based upon, and claims the benefit of and priority to, Chinese Patent Application No. 201810770314.8, filed on Jul. 13, 2018, the entire disclosure of which being hereby incorporated by reference as a part of the present application.

TECHNICAL FIELD

The present disclosure relates to the field of biomedical equipment and, more particularly, to a method for identifying arrhythmia, device for identifying arrhythmia, and computer readable medium.

BACKGROUND

During each cardiac cycle in a heart, the pacemaker, the atria, and the ventricle are excited one after another. The bioelectricity generated is an electrocardiogram (ECG) signal, which causes a potential change on the body surface that can be recorded by an electrocardiograph to form an electrocardiogram. Each cardiac cycle corresponds to a group of ECG waves, which appear as a P wave, a QRS complex, a T wave, etc. on the electrocardiogram. Due to fast and non-invasive characteristics, ECG detection technology provides a basis for primary diagnosis and treatment, and is widely used in clinical practice.

Recently, a variety of portable single-lead electrocardiographs have been developed having a small size, low cost, portability, and real-time or long-term heart-fluctuation monitoring functions.

SUMMARY

The present application provides a method for identifying arrhythmia, a device for identifying arrhythmia, and a computer readable medium.

To solve the above problem, the present application provides a method for identifying arrhythmia. The method includes:

acquiring a type of arrhythmia to be identified;

acquiring an electrocardiogram (ECG) signal collected by an ECG acquisition device;

detecting feature wave information in the ECG signal according to the type of arrhythmia to be identified;

extracting a feature parameter from the ECG signal and the feature wave information according to the type of arrhythmia to be identified; and identifying, by a classifier, an occurrence of the type of arrhythmia to be identified according to the feature parameter.

In some embodiments of the present disclosure, the classifier comprises one of: a neural network, a random forest, and a support vector machine.

In some embodiments of the present disclosure, the method further includes normalizing the extracted feature parameter after extracting the feature parameter from the ECG signal and the feature wave information according to the type of arrhythmia to be identified and before identifying, by the classifier, the occurrence of the type of arrhythmia to be identified according to the feature parameter.

In some embodiments of the present disclosure, the normalizing comprises but is not limited to the following methods: a linear proportional transformation method, a range conversion method, or a zero mean standardization method.

In some embodiments of the present disclosure, the normalizing comprises:

$$y_i = \frac{x_i - \min(x)}{\max(x) - \min(x)},$$

where $x_i$ is a normalized feature parameter to be processed, $\max(x)$ is a maximum value of the feature parameter, $\min(x)$ is a minimum value of the feature parameter, and $y_i$ is a normalized feature parameter.

In some embodiments of the present disclosure, the type of arrhythmia comprises normal or bundle branch block heartbeat, supraventricular abnormal heartbeat, ventricular abnormal heartbeat, ventricular fusion heartbeat and an unclassified heartbeat, and when the acquired type of arrhythmia to be identified is one of above types, the feature wave information includes QRS wave information, P wave information, and T wave information; and the extracted feature parameter includes a time domain feature parameter, a wavelet feature parameter, a frequency domain feature parameter, and a nonlinear feature parameter.

In some embodiments of the present disclosure, the QRS wave information, the P wave information, and the T wave information are detected using a threshold detection method, a template matching method, an adaptive threshold method, a wavelet transform method, or a morphology operator method.

In some embodiments of the present disclosure, the ECG signal is decomposed by four scales with a quadratic spline wavelet, and an R wave peak position is obtained by zero-crossing between a pair of positive and negative maximum values on a $2^3$ scale.

In some embodiments of the present disclosure, a starting point of Q wave is positioned at a third inflection point position before the R peak position on a $2^1$ scale.

In some embodiments of the present disclosure, an end point of an S wave is positioned at a third inflection point position after the R peak on a $2^1$ scale.

In some embodiments of the present disclosure, the P wave information is obtained by zero-crossing between a pair of positive and negative maximum values on a $2^4$ scale in a fixed window before the R wave peak.

In some embodiments of the present disclosure, T wave information is obtained by zero-crossing between a pair of positive and negative maximum values on a $2^4$ scale in a fixed window after the R wave peak.

In some embodiments of the present disclosure, when the type of arrhythmia to be identified is an atrial fibrillation, the feature wave information includes the R wave information and the P wave information; and the extracted feature parameter includes a wavelet feature parameter, a frequency domain feature parameter, and a time domain feature parameter.

In some embodiments of the present disclosure, the frequency domain feature parameter includes a feature parameter of a frequency band in which an f wave is located, and the time domain feature parameter includes an RR interval related feature parameter and the feature parameter representing a presence of a P wave within the heartbeat.

In some embodiments of the present disclosure, the ECG signal is decomposed by four scales with a quadratic spline wavelet, and the R wave peak position is obtained by zero-crossing between a pair of positive and negative maximum values on a $2^3$ scale.

In some embodiments of the present disclosure, P wave information is obtained by zero-crossing between a pair of positive and negative maximum values on a $2^4$ scale in a fixed window before the R wave peak position.

In some embodiments of the present disclosure, the method further includes: before the feature wave information in the ECG signal is detected according to the type of arrhythmia to be identified, preprocessing the ECG signal, the preprocessing comprising denoising.

The present application provides a device for identifying arrhythmia, including a processor and a memory having computer executable instructions stored thereon, wherein when the computer executable instructions are executed by the processor, the processor performs the method for identifying arrhythmia described above.

In some embodiments of the present disclosure, the ECG acquisition device is a single-lead ECG acquisition device.

The present application provides a computer readable medium having stored therein computer executable instructions. The computer executable instructions are executable to perform the method for identifying arrhythmia described above.

It should be understood that both the foregoing general description and the following detailed description are exemplary and explanatory only and are not restrictive of the disclosure.

BRIEF DESCRIPTION OF THE DRAWINGS

In order to more clearly illustrate the technical solutions of the embodiments of the present disclosure, the drawings of the embodiments will be briefly described below. Understandably, the drawings in the following description relate only to some embodiments of the present disclosure and do not limit the disclosure.

DETAILED DESCRIPTION

In order to make those skilled in the art better able to understand the technical solutions of the present application, the present application will be described in detail below with reference to the accompanying drawings and specific embodiments.

Various aspects and features of the present application are described herein with reference to the drawings.

These and other features of the present application will become apparent from the following description of preferred implementations of the embodiments, which are illustrated as non-limiting examples with reference to accompanying drawings.

It will also be appreciated that, although the present application has been described with reference to particular embodiments, many other equivalents of the present application can be contemplated by those skilled in the art to implement the present disclosure having features as set forth in the claims and the equivalents falling within the scope of protection defined thereby.

The above and other aspects, features, and advantages of the present disclosure will become more apparent from the aspects of the appended claims.

Specific embodiments of the present application will be described hereinafter with reference to the drawings; however, it should be understood that the embodiments of the present disclosure are merely examples of the present application, which can be implemented in various ways. Well-known and/or repetitive functions and structures are not described in detail in order to determine the real intention according to the user's operation history, and not to obscure the present application with unnecessary or redundant details. Therefore, the specific structural and functional details of the present disclosure are not intended to be limiting, but are merely used as a basis and representative basis of the claims to teach one skilled in the art to use the present disclosure in virtually any suitable detailed application.

The description may use the phrases "in one embodiment", "in another embodiment", "in still another embodiment", or "in other embodiments", which may refer to one or more of the same or different embodiments.

Figure 1:
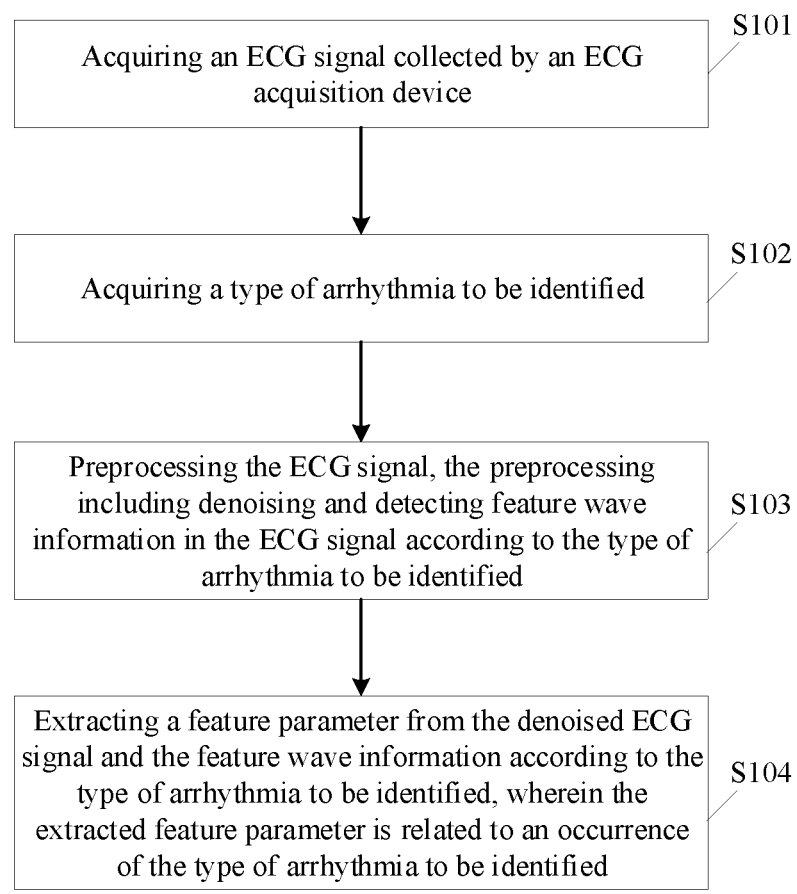
FIG. 1 illustrates a flowchart of a method for extracting a feature parameter identifying arrhythmia according to an embodiment of the present disclosure.

An embodiment of the present application provides a method for extracting a feature parameter of arrhythmia. As shown in FIG. 1, the method includes the following steps:

box S101, acquiring an ECG signal collected by an ECG acquisition device;

box S102, acquiring a type of arrhythmia to be identified;

box S103, preprocessing the ECG signal, the preprocessing including denoising and detecting feature wave information in the ECG signal according to the type of arrhythmia to be identified;

box S104, extracting a feature parameter from the denoised ECG signal and the feature wave information according to the type of arrhythmia to be identified, wherein the extracted feature parameter can be utilized with a classifier to identify the type of arrhythmia, i.e., the extracted feature parameter may be used to identify the occurrence of the type of arrhythmia to be identified according to the feature parameter.

In the embodiment of the present disclosure, the sequence of box S101 and box S102 is not specifically limited. Box S102 may be performed first, and then box S101 may be performed according to actual needs. In addition, in box S102, the type of the arrhythmia to be identified may be acquired by a setting operation of the user, a default value, or the like, and is not specifically limited herein. In addition, it should also be understood that in the case of using default values, box S102 can be omitted as needed.

In the above method for extracting a feature parameter of arrhythmia, feature wave information in the ECG signal can be detected according to different types of arrhythmia to be identified in a targeted manner, and according to the type of arrhythmia to be identified, a feature parameter is extracted from the denoised ECG signal and the feature wave information in a targeted manner, so that the detection of the feature wave information and the extraction of the feature parameter can be efficiently targeted, which avoids wasting resources on extracting redundancy or meaningless feature wave information and feature parameters. In addition, the feature parameter extracted by the above method may not be directly used to identify the type of arrhythmia.

At box S101, an ECG signal collected by an ECG acquisition device is acquired. In some embodiments of the present disclosure, the ECG signal may be an I-lead ECG signal or an II-lead ECG signal. In some embodiments of the present disclosure, the ECG acquisition device may be a single-lead ECG acquisition device, wherein the single-lead ECG acquisition device may be a single-lead electrocardiograph.

Specifically, the type of the ECG signal read out is determined by the specific form of the single-lead ECG acquisition device. The I-lead ECG signal is in a direction from the right hand to the left-hand. When the single-lead ECG device is a single-lead electrocardiograph, the single-lead electrocardiograph can be in the following form, such as a short-sleeved shirt or a vest, etc., with an electrode distribution direction being right shoulder-left shoulder, right arm-left arm, such as a neck-wearing necklace, a collar, a pendant, etc., with the electrode distribution direction being the right rear side of the neck—the left rear side of the neck, such as a hand-held card, a ring, a bracelet, a watch, etc., with the electrode distribution direction being right hand-left hand. For the card-type, the left hand and the right hand are required to contact the electrodes at the same time when acquiring signals, and for the form of a ring, a bracelet, a watch or the like, the finger not wearing anything is required to be placed on the electrode sensor, such as the ring, the bracelet, the watch or the like, when acquiring signals. The II-lead ECG signal is in the direction from the right hand to the left foot. When the single-lead ECG device is a single-lead electrocardiograph, the single-lead electrocardiograph can be in the following form, such as a clothing strap vest, an coverall, etc., with the electrode distribution direction being the right shoulder—the front side of the left waist, such as a chest-stick type, with the electrode distribution direction being the upper right chest—the lower left chest.

At box S102, a type of arrhythmia to be identified is acquired. As previously discussed, in box S102, the type of arrhythmia to be identified may be acquired by user settings, and in the event that the default value or other preset value is used, box S102 may be omitted. As an example, the type of arrhythmia includes at least one or more of: atrial fibrillation, normal or bundle block heartbeat, supraventricular abnormal heartbeat, ventricular abnormal heartbeat, ventricular fusion heartbeat, and an unclassified heartbeat. It makes it possible to perform the detection of the type of arrhythmia in a targeted manner when identifying the arrhythmia.

At box S103, the ECG signal is preprocessed, the preprocessing including denoising and detecting feature wave information in the ECG signal according to the type of arrhythmia to be identified. Specifically, when the acquired ECG signal is an I-lead ECG signal or an II-lead ECG signal, noise, such as low-frequency baseline drift, high-frequency myoelectric interference, and electrode interference, can be filtered out through a filter. As an example, the filter may be selected but not limited to the following types: a wavelet filter, a band pass filter, a morphological filter, and the like. In the present embodiment, denoising as part of the preprocessing can improve the quality of the electrocardiographic signal, thereby more accurately detecting the feature wave information and extracting the feature parameters in subsequent operations. However, it should be understood that denoising here is not an essential step. In some embodiments, such as when the quality of the ECG signal is not good enough or the required monitoring accuracy is not high, the denoising step can be omitted. In the following, taking wavelet decomposition filtering as an example, the wavelet decomposition can divide the ECG signal into 10 layers, and respectively sets the detail coefficients for the first and second layer corresponding to the high-frequency noise and the detail coefficients for the ninth and tenth layer corresponding to the low-frequency baseline drift to zero. Then, the processed wavelet detail coefficients is reconstructed to acquire the denoised ECG signal.

In some embodiments of the present disclosure, after the denoising process of the ECG signal is completed, the QRS complex, the P wave, and the T wave information may be detected from the denoised ECG signal.

Specifically, detecting the P wave, the QRS complex, and the T wave of the ECG signal may include, but is not limited to, performing the following methods: a threshold detection method, a template matching method, an adaptive threshold method, a wavelet transform method, a morphology operator method, and the like. Taking a quadratic spline wavelet decomposition method as an example, the ECG signal is decomposed by four scales with the quadratic spline wavelet, and the corresponding QRS complex energy distribution is the largest on the $2^3$ scale. On the $2^3$ scale, the R wave peak position may be obtained by zero-crossing between a pair of positive and negative maximum values. The Q wave and the S wave are high-frequency low-amplitude waves, and the energy is mainly concentrated on the $2^1$ scale. So the third inflection point position before the R peak position on the $2^1$ scale may be taken as the starting point of the Q wave, and the third inflection point position after the R peak may be taken as the end point of the S wave. The P wave and the T wave generally have low frequencies and amplitudes, and the energy is mainly concentrated on the $2^4$ scale. Therefore, the P wave information may be obtained by zero-crossing between a pair of positive and negative maximum values on the $2^4$ scale in a fixed window before the R wave peak, and the T wave information may be obtained by zero-crossing between the pair of positive and negative maximum values on the $2^4$ scale in a fixed window after the R wave peak.

At box S104, a feature parameter is extracted from the denoised ECG signal and the feature wave information according to the type of arrhythmia to be identified. As an example, the feature parameter may be selected, but not limited to, the following types: time domain features, frequency domain features, wavelet features, high order statistics features, nonlinear features, and the like. Specifically, the time domain feature parameter can be extracted from the QRS complex, the P wave and the T wave information. The time domain feature parameter can be selected but not limited to the following types: an RR interval, a QRS group width, an R wave amplitude, a presence or absence of a P wave, and so on. The extracted wavelet feature parameter may be selected from, but not limited to, the following types: wavelet detail coefficients, detail coefficient energy ratios, and the like. The extracted frequency domain features may be selected from, but not limited to, the following types: a frequency domain slope of the ECG signal, a harmonic number, an amplitude difference, a low frequency and high frequency energy ratio in the energy spectrum, and the like. The extracted nonlinear features may be selected from, but not limited to, the following types: an approximate entropy, a sample entropy, and the like. The extracted high order statistic features may be selected from, but not limited to, the following types: a second order statistic, a third order statistic, and the like.

When the type of arrhythmia to be identified changes, the type of feature parameter to be extracted in a targeted manner is also changed. In some embodiments of the present disclosure, in the case where the type of arrhythmia to be identified is a normal or bundle branch block heartbeat, a supraventricular abnormal heartbeat, a ventricular abnormal heartbeat, a ventricular fusion heartbeat, and an unclassified heartbeat, the feature wave information includes QRS wave information, P wave information, and T wave information; and the extracted feature parameters include a time domain feature parameter, a wavelet feature parameter, a frequency domain feature parameter, and a nonlinear feature parameter. In some embodiments of the present disclosure, when the type of arrhythmia to be identified is an atrial fibrillation, the feature wave information includes R wave information and the P wave information; and the extracted feature parameter includes the wavelet feature parameter, the frequency domain feature parameter, and the time domain feature parameter. In some embodiments of the present disclosure, the frequency domain feature parameter includes a feature parameter of a frequency band in which the f wave is located, and the time domain feature parameter includes a feature parameter related to the RR interval and a feature parameter that represents a presence of the P wave in the heartbeat.

At this time, when the type of the identified arrhythmia is atrial fibrillation, the corresponding feature wave information for detecting the atrial fibrillation heartbeat is extracted from the denoised ECG signal, and then, the corresponding feature parameter is extracted from the feature wave information in a targeted manner, to identify the atrial fibrillation.

In some embodiments of the present disclosure, after the feature parameter is extracted, the extracted feature parameter is normalized to identify the type of arrhythmia with the classifier.

Specifically, the extracted feature parameter is normalized, and the acquired feature parameter is scaled according to a proportion to fall into a small specific interval, such as [−1, 1] or [0, 1]. The normalization process can reduce the calculation amount while preventing the feature attribute having a relatively large initial range from being too heavy compared to the feature parameter having a relatively small initial range. The normalization method can be selected, but not limited to, the following methods: a linear proportional transformation method, a range conversion method, a zero mean standardization method, and the like. In the following, the normalization process will be described taking the range conversion method as an example:

$$y_i = \frac{x_i - \min(x)}{\max(x) - \min(x)},$$

where $x_i$ is a normalized feature parameter to be processed, $\max(x)$ is the maximum value of the feature parameter, $\min(x)$ is the minimum value of the feature parameter, and $y_i$ is the normalized feature parameter as the input of the classifier.

In the present embodiment, the method of extracting the characteristic parameters of the arrhythmia, according to the present disclosure, is specifically explained by the boxes S101, S102, S103, and S104, however, those skilled in the art should understand that in the present disclosure, the method is not limited to the above-described step division and execution order. Some of the boxes S101 to S104 above may occur simultaneously, in reverse order, and/or in a single step, or one or more of the steps may be performed in several sub-steps.

In addition, based on the above method for extracting a characteristic parameter of arrhythmia, an embodiment of the present disclosure provides a method for identifying an arrhythmia, wherein the method includes:

acquiring a type of arrhythmia to be identified;

acquiring an electrocardiogram (ECG) signal collected by an ECG acquisition device;

detecting feature wave information in the ECG signal, according to the type of arrhythmia to be identified;

extracting a feature parameter from the ECG signal and the feature wave information according to the type of arrhythmia to be identified; and identifying, by a classifier, the occurrence of the type of arrhythmia to be identified according to the feature parameter.

Figure 2:
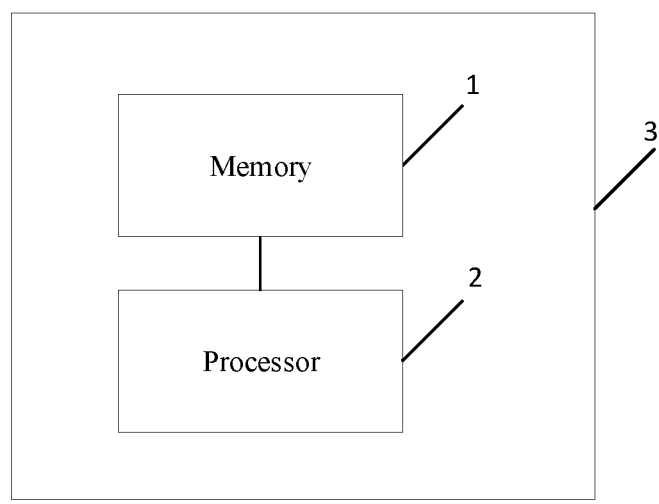
FIG. 2 illustrates a block diagram of a device for identifying arrhythmia according to an embodiment of the present disclosure.
Figure 3:
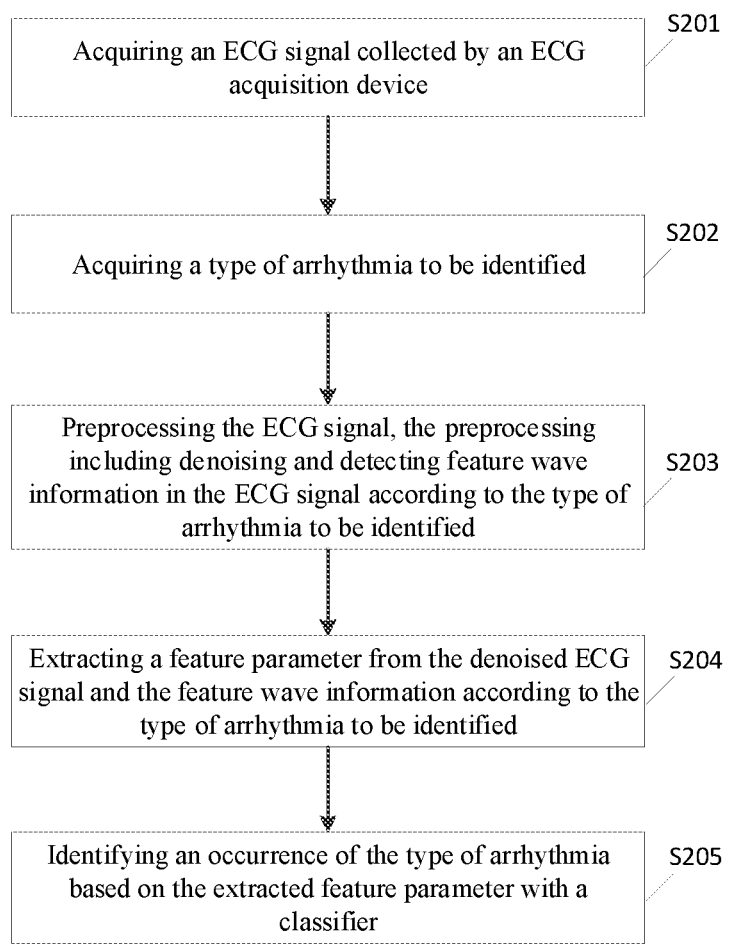
FIG. 3 illustrates a flowchart of various steps of a method for identifying arrhythmia implemented when computer-executable instructions are executed by a processor according to an embodiment of the present disclosure.

According to an embodiment of the present application, there is also provided a device 3 for identifying arrhythmia. As shown in FIG. 2, the device 3 includes a processor 2 and a memory 1 for storing computer executable instructions thereon. When the processor 2 executes the computer executable instructions, the processor 2 performs an instance of a method for identifying arrhythmia as shown in FIG. 3, which may include the following steps:

box S201, acquiring an ECG signal collected by an ECG acquisition device according to the above method for extracting a feature information of arrhythmia; box S202, acquiring and/or setting a type of arrhythmia to be identified; box S203, preprocessing the ECG signal, the preprocessing including denoising and detecting feature wave information in the ECG signal according to the type of arrhythmia to be identified; and box S204, extracting a feature parameter from the denoised ECG signal and the feature wave information according to the type of arrhythmia to be identified; and box S205, identifying an occurrence of the type of arrhythmia based on the extracted feature parameter with a classifier.

The above device for identifying arrhythmia can detect feature wave information in the ECG signal in a targeted manner depending on the type of arrhythmia to be identified and then, extract a feature parameter in a targeted manner from the denoised ECG signal and the feature wave information according to the type of arrhythmia to be identified. Therefore, the detection of the feature wave information and the extraction of the feature parameter can be efficient and targeted, which can avoid wasting resources on extracting redundancy or meaningless feature wave information and feature parameters for identifying the type of arrhythmia. As such, it can improve the accuracy and efficiency for identifying the type of arrhythmia and provide technical support for the early identification of arrhythmia.

In some embodiments of the present disclosure, the processor 2 may be a processing device including one or more general purpose processing devices, such as a microprocessor, a central processing unit (CPU), a graphics processing unit (GPU), an accelerated processing unit (APU), and the like. More specifically, the processor 2 may be a Complex Instruction Set Computing (CISC) microprocessor, a Reduced Instruction Set Computing (RISC) microprocessor, a Very Long Instruction Word (VLIW) microprocessor, a processor implementing other instruction sets, or a processor that implements a combination of instruction sets. The processor 2 may also be one or more dedicated processing devices, such as an application specific integrated circuit (ASIC), a field programmable gate array (FPGA), a digital signal processor (DSP), a system on a chip (SOC), and the like. As will be appreciated by those skilled in the art, in some embodiments, the processor 2 can be a dedicated processor rather than a general purpose processor. The processor 2 may include one or more well-known processing devices, such as a Pentium™, Core™, Xeon™, or Itanium® series of microprocessors manufactured by Intel™, Turion™, Athlon™, Sempron™, Opteron™, FX™, Phenom™ series microprocessors manufactured by AMP™, or any of a variety of processors manufactured by Sun Microsystems. The processor 2 may also include an acceleration processing unit, such as the desktop A-4 (6, 8) Series™ manufactured by AMD™, and the Xeon Phi™ series manufactured by Intel™. The disclosed embodiments are not limited to any type of processor(s) that are otherwise configured to satisfy the computing demand for identification, analysis, maintenance, generation, and/or provision of a large amount of ECG signal data or processing such ECG signal data, or otherwise configured to process any other type of data consistent with the disclosed embodiments. Moreover, the term "processor" can include more than one processor, such as a multi-core design or multiple processors each having a multi-core design. The processor 2 can execute a sequence of computer program instructions stored in the memory 1 to perform the various operations, processes, methods described in greater detail herein.

For example, the memory 1 can include any combination of one or more computer program products, which can include various forms of computer readable storage media, such as a volatile memory and/or a nonvolatile memory. The volatile memory can include, for example, a random access memory (RAM) and/or a cache and the like. The nonvolatile memory may include, for example, a read only memory (ROM), a hard disk, an erasable programmable read only memory (EPROM), a portable compact disk read only memory (CD-ROM), a USB memory, a flash memory, and the like.

Thereafter, a type of arrhythmia is identified based on the extracted feature parameter with a classifier. The classifier can be selected, but not limited to, the following types: a neural network, a random forest, a support vector machine, and the like.

The ECG signal is classified by taking the normalized feature parameter as an input to the classifier. For example, utilizing a support vector machine, a specific percentage such as 80% of the data is selected as a training set, and the remaining 20% of the data is taken as a test set, with the training set and the test set having no redundant data.

Figure 4:
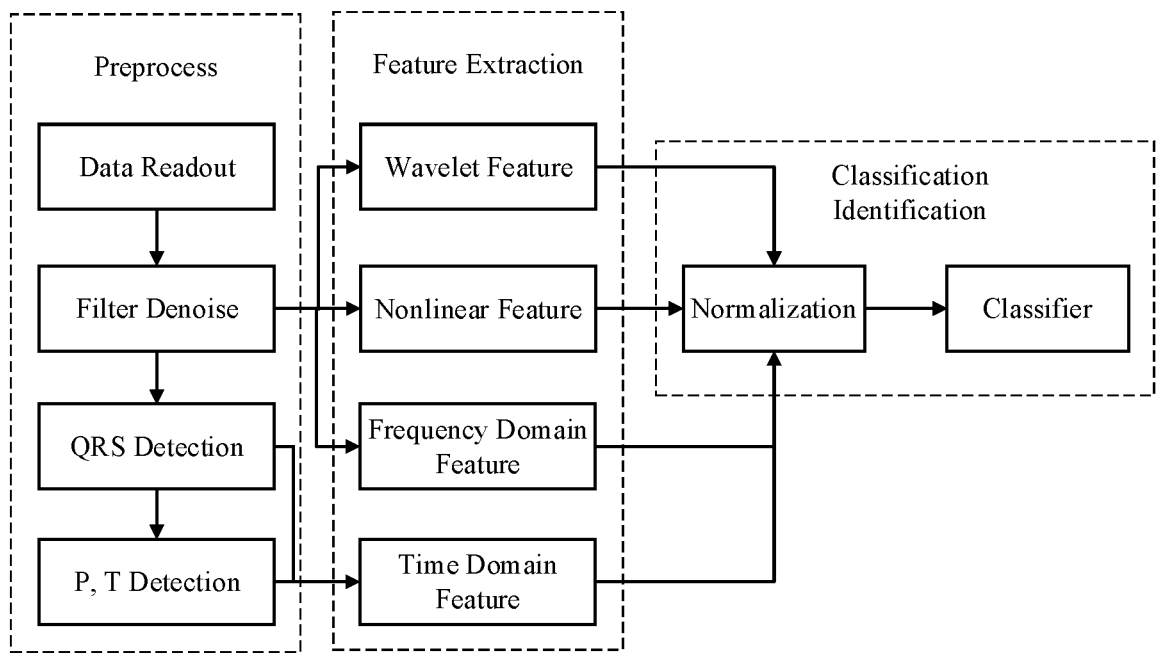
FIG. 4 is a flowchart of a process for identifying 5 types of arrhythmia (5 types of labels) in accordance with the AAMI standard from an ECG signal according to an embodiment of the present disclosure.

The classification mode may be classifying heartbeat by heartbeat, in which a single heartbeat is taken as one sample, or an ECG signal of a variable length is taken as one sample. Here, for example, the MIT-BIH arrhythmia database is used as a data set for classifying heartbeat by heartbeat. There are a total of 48 patients, from which a total of 102,840 heartbeat samples are taken. According to the AAMI standard, the database labels are divided into five types, and the types and the corresponding sample numbers are shown in the table. The flowchart of the process of identifying the five types of arrhythmia (5 types of labels) according to the AAMI standard from the ECG signal may refer to FIG. 4.

Specifically, the five types of arrhythmia are: N-normal or bundle branch block heartbeat, S-supraventricular abnormal heartbeat, V-ventricular abnormal heartbeat, F-ventricular fusion heartbeat, and Q-unclassified heartbeat. Among them, the subtypes of the 5 types of arrhythmia are: N—normal heartbeat, L—left bundle branch block, R—right bundle branch block, e-atrial escape, j-boundary escape, A-atrial premature beats, a-abnormal atrial premature beats, J—border premature beats, S—supraventricular premature beats or ectopic beats, V—ventricular premature contractions, E—ventricular escape, F—ventricular fusion heartbeat, P—pacemaker heartbeat, f—pacing fusion heartbeat, Q—unclassified heartbeat. The correspondence and distribution quantity of various arrhythmia types (subtypes) in the 102840 heartbeat samples taken out are shown in Table 1.

TABLE 1

Correspondence and distribution of various arrhythmia types (subtypes) in heartbeat samples

| Type | N | S | V | F | Q |
| --- | --- | --- | --- | --- | --- |
| Subtype | N, L, R, e, j | A, a, J, S | V, E | F | P, f, Q |
| Quantity | 86021 | 2610 | 5461 | 784 | 7964 |

The classifier is supervised and trained with 80% of the heartbeat samples labeled above.

The remaining 20% of the data is taken as a test set and is tested with the trained classifier. The overall accuracy of the test results is 96.9%, and the precision and recall rate of each type is shown in Table 2.

TABLE 2 precision and recall rate of various types of arrhythmia in test set of heart rate samples

| Type | N | S | V | F | Q |
| --- | --- | --- | --- | --- | --- |
| Precision | 97.3 | 74.7 | 96.1 | 92.9 | 98.7 |
| Recall Rate | 99.2 | 52.7 | 89.4 | 66.9 | 94.2 |

There is no atrial fibrillation in the MIT-BIH arrhythmia database mentioned above, but the detection of atrial fibrillation, especially paroxysmal atrial fibrillation, is of great significance for intelligent diagnosis and treatment.

Figure 5:
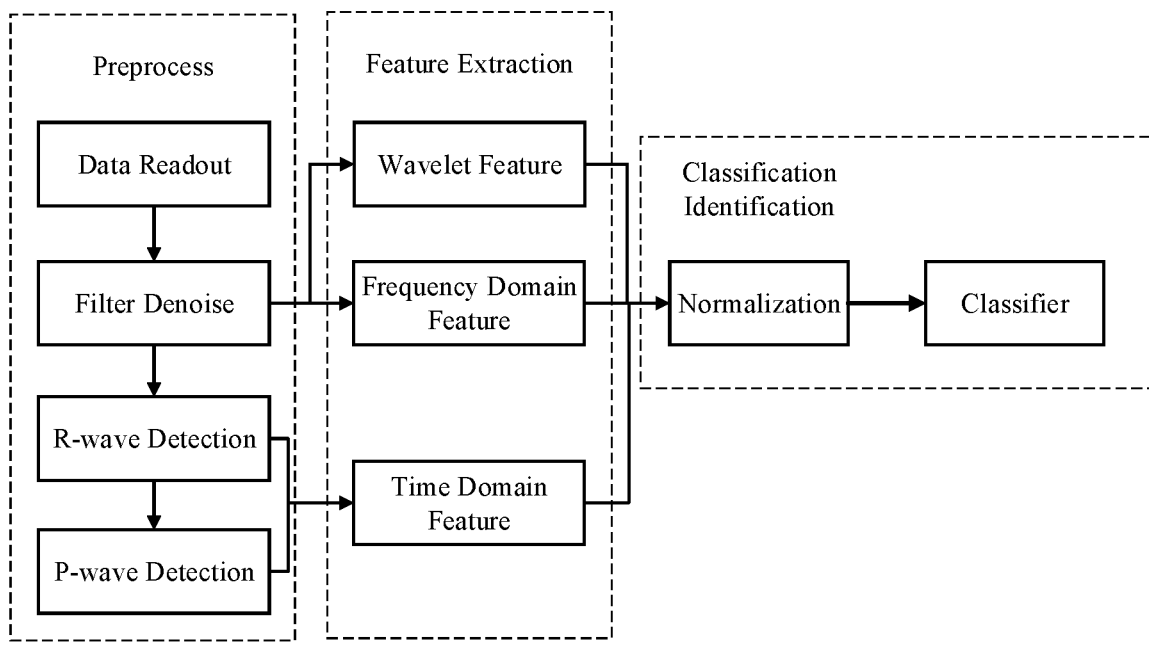
FIG. 5 is a flowchart of a process for identifying atrial fibrillation heartbeat from an ECG signal according to an embodiment of the present disclosure.

In some embodiments of the present disclosure, in the case that the type of arrhythmia to be identified is atrial fibrillation, the details may refer to FIG. 5.

The feature wave information includes R wave information and P wave information.

The extracted feature parameter includes a wavelet feature parameter, a frequency domain feature parameter, and a time domain feature parameter.

Further, in some embodiments of the present disclosure, the frequency domain feature parameter includes a feature parameter of a frequency band in which the f wave is located, and the time domain feature parameter includes a feature parameter related to the RR interval and a presence of a P wave in the heartbeat.

As an example, in the feature parameter of the frequency band in which the f wave is located, the frequency of the f wave is generally 350-600 beats/min. In the following, the atrial fibrillation is identified in a classification mode taking ECG signal of a variable length as a sample. The specific process is as follows.

1. The ECG signal is read out. The ECG signal is generally an I-lead ECG signal or an II-lead ECG signal, and the ECG signal length is generally not shorter than 10 seconds, no longer than 1 minute. The ECG signal is filtered to remove low frequency baseline drift and high frequency interference noise. The position of the ECG R wave peak is detected. The P wave is detected in a specific window before the R wave peak position.

2. A wavelet feature is detected from a denoised ECG signal, including a wavelet detail coefficient and a detail coefficient energy ratio. A frequency domain feature is extracted from the denoised ECG signal, including an energy ratio of frequency band in which an f wave is located. An RR interval relevant feature is extracted with the detected R-peak position, including a RR interval, an R wave amplitude, a RR interval difference value, and the mean, standard deviation, median, maximum, minimum, and quantile of a feature such as the RR interval. The P wave position is used to obtain whether there is a P wave in each heartbeat, and a proportion of the heartbeats in which there is no P wave against the total heartbeat in the input ECG signal of a variable length.

3. The wavelet feature, the frequency domain feature and the RR interval feature extracted in step 2 are normalized and then, are input together with the P wave feature to the classifier to identify the atrial fibrillation. The output result is whether a suspected atrial fibrillation is detected from the segment of ECG signal.

An embodiment of the present disclosure further provides a non-transitory computer-readable medium. The readable medium stores computer executable instructions, and when the computer executable instructions are executed, a method for identifying arrhythmia as shown in FIG. 3 can be implemented, which may include the following steps:

box S201, acquiring an ECG signal collected by an ECG acquisition device;

box S202, setting a type of arrhythmia to be identified;

box S203, preprocessing the ECG signal, the preprocessing including denoising and detecting feature wave information in the ECG signal according to the type of arrhythmia to be identified;

box S204, extracting a feature parameter from the denoised ECG signal and the feature wave information according to the type of arrhythmia to be identified; and box S205, identifying an occurrence of the type of arrhythmia based on the extracted feature parameter with a classifier.

The computer readable storage medium can take a variety of forms including, but not limited to, for example, a volatile memory, and/or a nonvolatile memory. The volatile memory can include, for example, a random access memory (RAM) and/or a cache and the like. The non-volatile memory may include, for example, a read only memory (ROM), a hard disk, an erasable programmable read only memory (EPROM), a portable compact disk read only memory (CD-ROM), a USB memory, a flash memory, and the like.

In some embodiments of the present disclosure, after the feature parameter is extracted, the extracted feature parameter is normalized to identify the type of arrhythmia with the classifier.

In some embodiments of the present disclosure, in the case where the type of arrhythmia to be identified is a normal or a bundle branch block heartbeat, a supraventricular abnormal heartbeat, a ventricular abnormal heartbeat, a ventricular fusion heartbeat, and an unclassified heartbeat, the feature wave information includes QRS wave information, P wave information, and T wave information; and the extracted feature parameter include a time domain feature parameter, a wavelet feature parameter, a frequency domain feature parameter, and a nonlinear feature parameter.

In some embodiments of the present disclosure, in a case where the type of arrhythmia to be identified is an atrial fibrillation, the feature wave information includes R wave information and P wave information, and the extracted feature parameter includes a wavelet feature parameter, a frequency domain feature parameter, and a time domain feature parameter.

In some embodiments of the present disclosure, the frequency domain feature parameter includes a feature parameter of a frequency band in which the f wave is located, and the time domain feature parameter includes a feature parameter related to the RR interval and a feature parameter that represents a presence condition of the P wave in the heartbeat.

It can be seen from the above that in the computer readable medium for identifying arrhythmia, the feature wave information in the ECG signal can be detected according to different types of arrhythmia to be identified in a targeted manner, and further according to the type of arrhythmia to be identified, the feature parameter is extracted from the denoised ECG signal, and the feature wave information in a targeted manner, so that the detection of the feature wave information and the extraction of the feature parameter can be efficient and targeted, which can avoid wasting resources on extracting redundancy or meaningless feature wave information and feature parameters for identifying the type of arrhythmia. Correspondingly, it can improve the accuracy and efficiency for identifying the type of arrhythmia and provide technical support for the early identification of arrhythmia.

The above embodiments are merely exemplary embodiments of the present application and are not intended to limit the present application, and the scope of protection of the present application is defined by the claims. A person skilled in the art can make various modifications or equivalents to the present application within the spirit and scope of the present application, and such modifications or equivalents are also considered to fall within the scope of the present application.

What is claimed is:

1. A computer-implemented method for identifying arrhythmia performed by at least one computing device having at least one hardware processor through execution of program instructions stored in memory, comprising:

acquiring a type of arrhythmia to be identified;

acquiring an electrocardiogram (ECG) signal collected by an ECG acquisition device;

detecting feature wave information in the ECG signal according to the type of arrhythmia to be identified;

extracting feature parameters from the ECG signal and the feature wave information according to the type of arrhythmia to be identified;

identifying, by a classifier, an occurrence of the type of arrhythmia to be identified according to the feature parameters;

wherein, in an instance in which the type of arrhythmia to be identified as acquired is one of a normal or bundle branch block heartbeat, a supraventricular abnormal heartbeat, a ventricular abnormal heartbeat, a ventricular fusion heartbeat, and an unclassified heartbeat:

the feature wave information comprises QRS wave information, P wave information, and T wave information; and extracted feature parameters comprise a time domain feature parameter, a wavelet feature parameter, a frequency domain feature parameter, and a nonlinear feature parameter;

wherein, in an instance in which the type of arrhythmia to be identified as acquired is an atrial fibrillation:

the feature wave information only comprises R wave information and P wave information;

extracted feature parameters only comprise a wavelet feature parameter, a frequency domain feature parameter, and a time domain feature parameter, wherein the wavelet feature parameter comprises a wavelet detail coefficient and a detail coefficient energy ratio, the frequency domain feature parameter comprises an energy ration of a frequency band in which an f wave is located, and the time domain feature parameter comprises an RR interval related feature parameter and a P wave feature parameter, and the RR interval related feature parameter comprises a RR interval, an R wave amplitude, a RR interval difference value, the P wave feature parameter is used for representing a presence of a P wave, and comprises a P wave position and a proportion of heartbeats in which no P wave exists against a total heartbeat in the ECG signal; and the wavelet feature, the frequency domain feature and the RR interval feature are normalized, and input together with the P wave feature to the classifier to identify the atrial fibrillation; and displaying information relating to the occurrence of the type of arrhythmia as identified on a display device.

2. The method for identifying arrhythmia according to claim 1, wherein the classifier comprises one of: a neural network, a random forest, and a support vector machine.

3. The method for identifying arrhythmia according to claim 1, wherein the feature parameters as extracted are normalized by: a linear proportional transformation method, a range conversion method, or a zero mean standardization method.

4. The method for identifying arrhythmia according to claim 1, wherein the feature parameters as extracted are normalized by determining:

$$y_i = \frac{x_i - \min(x)}{\max(x) - \min(x)},$$

where $x_i$ is a normalized feature parameter to be processed, $\max(x)$ is a maximum value of the feature parameters, $\min(x)$ is a minimum value of the feature parameters, and $y_i$ is a normalized feature parameter.

5. The method for identifying arrhythmia according to claim 1, wherein the QRS wave information, the P wave information, and the T wave information are detected using a threshold detection method, a template matching method, an adaptive threshold method, a wavelet transform method, or a morphology operator method.

6. The method for identifying arrhythmia according to claim 1, wherein:

the ECG signal is decomposed by four scales with a quadratic spline wavelet;

an R wave peak position is obtained by zero-crossing between a pair of positive and negative maximum values on a $2^3$ scale; and a starting point of a Q wave is positioned at a third inflection point position before the R wave peak position on a $2^1$ scale and an end point of an S wave is positioned at a third inflection point position after the R wave peak position on a $2^1$ scale.

7. The method for identifying arrhythmia according to claim 6, wherein the P wave information is obtained by zero-crossing between a pair of positive and negative maximum values on a $2^4$ scale in a fixed window before the R wave peak position.

8. The method for identifying arrhythmia according to claim 6, wherein the T wave information is obtained by zero-crossing between a pair of positive and negative maximum values on a $2^4$ scale in a fixed window after the R wave peak position.

9. The method for identifying arrhythmia according to claim 1, further comprising:

before the feature wave information in the ECG signal according to the type of arrhythmia to be identified is detected, preprocessing the ECG signal, the preprocessing comprising denoising.

10. A device for identifying arrhythmia, comprising:

at least one hardware processor and a memory having computer executable instructions stored thereon, wherein, when the computer executable instructions are executed by the processor, the processor performs a method comprising:

acquiring a type of arrhythmia to be identified;

acquiring an electrocardiogram (ECG) signal collected by an ECG acquisition device;

detecting feature wave information in the ECG signal according to the type of arrhythmia to be identified;

extracting feature parameters from the ECG signal and the feature wave information according to the type of arrhythmia to be identified;

identifying, by a classifier, an occurrence of the type of arrhythmia to be identified according to the feature parameters;

wherein, in an instance in which the type of arrhythmia to be identified as acquired is one of a normal or bundle branch block heartbeat, a supraventricular abnormal heartbeat, a ventricular abnormal heartbeat, a ventricular fusion heartbeat, and an unclassified heartbeat:

the feature wave information comprises QRS wave information, P wave information, and T wave information; and extracted feature parameters comprise a time domain feature parameter, a wavelet feature parameter, a frequency domain feature parameter, and a non-linear feature parameter;

wherein, in an instance in which the type of arrhythmia to be identified as acquired is an atrial fibrillation:

the feature wave information only comprises R wave information and P wave information;

extracted feature parameters only comprise a wavelet feature parameter, a frequency domain feature parameter, and a time domain feature parameter, wherein the wavelet feature parameter comprises a wavelet detail coefficient and a detail coefficient energy ratio, the frequency domain feature parameter comprises an energy ration of a frequency band in which an f wave is located, and the time domain feature parameter comprises an RR interval related feature parameter and a P wave feature parameter, and the RR interval related feature parameter comprises a RR interval, an R wave amplitude, a RR interval difference value, the P wave feature parameter is used for representing a presence of a P wave, and comprises a P wave position and a proportion of heartbeats in which no P wave exists against a total heartbeat in the ECG signal; and the wavelet feature, the frequency domain feature and the RR interval feature are normalized, and input together with the P wave feature to the classifier to identify the atrial fibrillation; and displaying information relating to the occurrence of the type of arrhythmia as identified on a display device.

11. The device for identifying arrhythmia according to claim 10, wherein the ECG acquisition device is a single-lead ECG acquisition device.

12. A non-transitory computer-readable medium having stored therein computer executable instructions, wherein the computer executable instructions are executable by a processor to perform a method comprising:

acquiring a type of arrhythmia to be identified;

acquiring an electrocardiogram (ECG) signal collected by an ECG acquisition device;

detecting feature wave information in the ECG signal according to the type of arrhythmia to be identified;

extracting feature parameters from the ECG signal and the feature wave information according to the type of arrhythmia to be identified;

identifying, by a classifier, an occurrence of the type of arrhythmia to be identified according to the feature parameters;

wherein, in an instance in which the type of arrhythmia to be identified as acquired is one of a normal or bundle branch block heartbeat, a supraventricular abnormal heartbeat, a ventricular abnormal heartbeat, a ventricular fusion heartbeat, and an unclassified heartbeat:

the feature wave information comprises QRS wave information, P wave information, and T wave information; and extracted feature parameters comprise a time domain feature parameter, a wavelet feature parameter, a frequency domain feature parameter, and a nonlinear feature parameter;

wherein, in an instance in which the type of arrhythmia to be identified as acquired is an atrial fibrillation:

the feature wave information only comprises R wave information and P wave information; and extracted feature parameters only comprise a wavelet feature parameter, a frequency domain feature parameter, and a time domain feature parameter, wherein the wavelet feature parameter comprises a wavelet detail coefficient and a detail coefficient energy ratio, the frequency domain feature parameter comprises an energy ration of a frequency band in which an f wave is located, and the time domain feature parameter comprises an RR interval related feature parameter and a P wave feature parameter, and the RR interval related feature parameter comprises a RR interval, an R wave amplitude, a RR interval difference value, the P wave feature parameter is used for representing a presence of a P wave, and comprises a P wave position and a proportion of heartbeats in which no P wave exists against a total heartbeat in the ECG signal; and the wavelet feature, the frequency domain feature and the RR interval feature are normalized, and input together with the P wave feature to the classifier to identify the atrial fibrillation; and displaying information relating to the occurrence of the type of arrhythmia as identified on a display device.

* * * * *